United States Patent [19]
Coates

[11] Patent Number: 5,814,037
[45] Date of Patent: Sep. 29, 1998

[54] TAILORED AND PROTECTIVE UNDERGARMENTS

[75] Inventor: Fredrica V. Coates, Earlysville, Va.

[73] Assignee: Tailored Technologies, Inc., Earlysville, Va.

[21] Appl. No.: 704,065

[22] Filed: Aug. 28, 1996

Related U.S. Application Data

[63] Continuation of Ser. No. 639,145, Apr. 29, 1996, Pat. No. 5,707,364, which is a continuation of Ser. No. 207,485, Mar. 7, 1994, abandoned, which is a continuation-in-part of Ser. No. 104,700, Aug. 11, 1993, Pat. No. 5,409,476.

[51] Int. Cl.$^6$ ...................................................... A61F 13/15
[52] U.S. Cl. .................... 604/393; 604/385.2; 604/397; 604/385.1
[58] Field of Search ................................ 604/358, 385.1, 604/385.2, 393, 394, 397

[56] References Cited

U.S. PATENT DOCUMENTS

| Re. 28,483 | 7/1975 | Ralph . |
|---|---|---|
| 731,201 | 6/1903 | Miller et al. . |
| 1,989,283 | 1/1935 | Limacher . |
| 2,545,761 | 3/1952 | Brink . |
| 2,558,215 | 6/1951 | Habig et al. . |
| 2,571,577 | 10/1951 | Howard . |
| 2,684,677 | 7/1954 | Pinney . |
| 2,743,725 | 5/1956 | Mathews . |
| 3,183,909 | 5/1965 | Roehr . |
| 3,349,769 | 10/1967 | Piekarski . |
| 3,383,693 | 5/1968 | Kahn et al. . |
| 3,386,443 | 6/1968 | Goldstein . |
| 3,563,242 | 2/1971 | Hedstrom . |
| 3,568,676 | 3/1971 | Guercio . |
| 3,653,381 | 4/1972 | Warnken . |
| 3,742,953 | 7/1973 | Lee . |
| 3,955,575 | 5/1976 | Okuda . |
| 4,020,843 | 5/1977 | Kandall . |
| 4,315,508 | 2/1982 | Bolick . |
| 4,425,128 | 1/1984 | Motomura . |
| 4,475,912 | 10/1984 | Coates . |
| 4,537,591 | 8/1985 | Coates . |
| 4,578,073 | 3/1986 | Dysart et al. . |
| 4,680,030 | 7/1987 | Coates et al. . |
| 4,681,581 | 7/1987 | Coates . |
| 4,685,909 | 8/1987 | Berg et al. . |
| 4,695,278 | 9/1987 | Lawson . |
| 4,704,117 | 11/1987 | Mitchell . |
| 4,728,326 | 3/1988 | Gilles . |
| 4,747,846 | 5/1988 | Boland et al. . |
| 4,773,906 | 9/1988 | Krushel . |
| 4,801,298 | 1/1989 | Sorenson et al. . |
| 4,808,177 | 2/1989 | DesMarais et al. . |
| 4,850,987 | 7/1989 | Gilomen . |
| 4,904,251 | 2/1990 | Igaue et al. . |
| 4,961,736 | 10/1990 | McCloud . |
| 4,994,037 | 2/1991 | Bernardin . |

(List continued on next page.)

FOREIGN PATENT DOCUMENTS

0 475 702  3/1992  European Pat. Off. .

Primary Examiner—John G. Weiss
Assistant Examiner—Dennis Ruhl
Attorney, Agent, or Firm—McDermott, Will & Emery

[57] ABSTRACT

A tailored diaper or diaper cover is constructed of a waterproof diaper shell enclosing an elongated sling of waterproof material having its upper and lower ends attached to, and its opposite sides free and floating on, the shell. A fluid absorbent pad on the inner surface of the sling is circumscribed by the waterproof material of the sling so as to establish a channel to entrap and isolate fluid from the shell. The lines of attachment between the waterproof and fluid absorbent materials at the upper and lower ends of the sling are arcuate, and the periphery of the sling is covered by elastic trim, causing the sling and pad to cup the pubis of a user when the diaper is worn. Entrapment of fluid within the sling may be enhanced by jell pad inserts. A washable pad of novel "butterfly" construction within the diaper or diaper cover enhances fluid absorption and drying. Another aspect of this invention provides embodiments of a tailored urinal for men, having a novel fluid containment bag and adapted to reside within underwear.

5 Claims, 9 Drawing Sheets

U.S. PATENT DOCUMENTS

| | | |
|---|---|---|
| 5,009,649 | 4/1991 | Goulter et al. . |
| 5,069,672 | 12/1991 | Wippler et al. . |
| 5,074,853 | 12/1991 | Bryant . |
| 5,106,382 | 4/1992 | Henry . |
| 5,112,324 | 5/1992 | Wallace . |
| 5,112,326 | 5/1992 | Quadrini . |
| 5,137,526 | 8/1992 | Coates ................................. 604/391 |
| 5,167,653 | 12/1992 | Igaue et al. . |
| 5,205,298 | 4/1993 | Hurst . |
| 5,209,743 | 5/1993 | Hardison . |
| 5,217,447 | 6/1993 | Gagnon . |
| 5,246,431 | 9/1993 | Minetola et al. . |
| 5,368,585 | 11/1994 | Dokken . |
| 5,403,303 | 4/1995 | Beplate ................................. 604/394 |
| 5,409,476 | 4/1995 | Coates . |

TAILORED AND PROTECTIVE UNDERGARMENTS

CROSS-REFERENCE TO RELATED APPLICATIONS

This application is a continuation of application Ser. No. 08/639,145 filed Apr. 29, 1996, now U.S. Pat. No. 5,707,364, which is a continuation of application Ser. No. 08/207,485 filed May 7, 1994, now abandoned which is a continuation-in-part of application Ser. No. 08,104,700 filed Aug. 11, 1993 and now U.S. Pat. No. 5,409,476.

TECHNICAL FIELD

This invention relates generally to the field of protective undergarments, such as adult and infant diapers, protective underwear and urinals, and more particularly to novel reusable or disposable fluid containment structures and manufacturing methods therefor.

BACKGROUND ART

Disposable diapers are in widespread use throughout the world as a result of their convenience. Although improvement has been made in the fluid absorbing characteristics of disposable diapers, leakage problems still remain, particularly at the leg holes. Disposable diapers are not tailored, and the appearance of disposable diapers is not appealing to most adult users.

The greatest problem with disposable diapers is the burden they place on our ecology, contributing substantially to waste that must be processed by municipalities. Despite the convenience of disposability, there is a ecological need to return to less waste producing undergarment systems both for infant and adult. Most prior art has concentrated on improvement of the disposable diaper rather than combining the elements of disposable and reusable undergarment systems.

Recent prior art has produced many significant advances in the field of reusable adult and infant diapers. In U.S. Pat. No. 4,475,912, issued on Oct. 4, 1984, a cloth diaper is configured to "grow" with an infant from birth to toddler, through unique placement of filamentary-type fasteners and folding of fabric upon which the fasteners are sewn. Recognizing the tendency of the hook-type material within filamentary fasteners to accumulate with lint, and become unusable following washings, U.S. Pat. No. 4,537,591 was directed to an improvement on hook and loop fasteners for cloth diapers, incorporating a protective cover to self-close filamentary fasteners during washing. U.S. Pat. No. 4,681,581, issued Jul. 25, 1987, discloses various embodiments for fastening diapers, reducing the cost of manufacturing. In U.S. Pat. No. 4,680,030, issued on Jul. 14, 1987, various configurations of hook and loop filamentary fasteners, arranged on fabric flaps of material, enable the diapers to withstand institutional washing conditions, high temperatures and chemicals. U.S. Pat. No. 5,137,526, issued on Aug. 11, 1992, is directed to methods of diaper construction such that fluids issuing from the wearer's pubis area are contained and encased within the diaper. This patent also describes improved methods of construction presenting the diaper with a more finished appearance while reducing costs. Co-pending application Ser. No. 08/104,700, filed on Aug. 11, 1993, teaches a novel construction of "sling" portions of reusable diapers for retaining fluid absorbent pads to the pubis.

The present invention represents improvement upon the aforenoted technology to more effectively fit the fluid producing area of the pubic region, isolating the pubis from the wearer's legs. The instant invention encases fluid just to the wearer's pubis area hence away from the legs, pelvis area, clothing and surrounding bedding.

An additional aspect of this invention encompasses tailored urinals, that is, vessels for containing the passage of fluid from a bedridden or mobile individual. Such vessels have previously been served by relatively cumbersome garment devices, disposable bedpads, and bedpans made of rubber, metal or plastic materials. Hard rubber, metal or plastic urinals are unable to conform to the shape of the body, and spilling is inevitable. Hence, these bedpans allow the spread of moisture to the rest of the body. Spreading of moisture occurs quickly, making the patient feel uncomfortable and creating considerable extra work for his or her caretaker.

Garment-type urinals, like typical cloth diapers, are somewhat ineffective as a result of leakage through the leg holes where most of the fluid escapes to the bed and clothing. The fitted condom-type rubber or bag-type devices designed for men provide some increase in effectiveness, however these are difficult to attach to allow fluid to drain off, a process usually involving clumsy tubes running from the receptacle into a larger receptacle for emptying. If the urinal is hand-held, a skillful caretaker is required or spilling is inevitable. This process can be embarrassing and uncomfortable for the male wearer.

Goulter, U.S. Pat. No. 5,009,649, Hurst, U.S. Pat. No. 5,205,298, Wallace, U.S. Pat. No. 5,112,324, Bryant, U.S. Pat. No. 5,074,853, Lee, U.S. Pat. No. 3,742,953 and Pouch, U.S. Pat. No. 824,634 disclose urinals fitted to the male anatomy. However, these urinals are not tailored to a garment without the drain-off tubing and such urinals are not easily handled by the user caring for himself.

Recently, there have been substantial improvements in disposable diaper technology by implementing the use of chemical gels placed in the central portion of those diapers. When technology of this nature is used, the remainder of the disposable diaper does not become wet, for the gelling action is so efficient it consolidates the fluid to a small localized area between the legs. Disposable pad inserts carrying the gel material are also available, examples being marketed under the brand name "Fitti" or "Diaper Doubler." When chemical gels are placed in an insert for absorption, the remainder of the disposable diaper in effect becomes useless and uncomfortable. Furthermore, the portion of the garment carrying the gel tends to slip about. I am not aware of any technology incorporating these gel pad inserts within tailored vessels for securing of the pads against the pubis for an absolutely stationary and secure fit without slipping.

Sanitary napkins have been provided within panties, but these napkins, or disposable pads, are generally backed with plastic and adhesive. It is commonly known that an imperfect fit results, and pads do not stay in place, with or without an adhesive. Pads that slip in panties, whether used for absorbing urine or blood, cause devastating accidents and embarrassment for the wearer. This slipping of the pad usually is due to an excessive amount of movement in that area of the body where the legs attach to the pubis area. Hence the pull or motion of the legs dislodges the pad.

In the prior art, reusable pads are retained in and attached to garments, but without tailoring to fit human anatomy. To stabilize pad movement, conventional pockets such as disclosed in Wippler, U.S. Pat. No. 5,069,692 have been taught. The pocket placed in the rear or any portion of the garment represents high risk for entrapping feces, creating difficulty in cleaning and possible bacterial growth.

Furthermore, because reusable pads do not contain gel, they must be relatively thick to absorb sufficient fluid for heavy use. These pads, however, are not easily cleaned, and drying requires a considerable amount of time and consumption of energy. The thicker the pad, the more difficult and costly the cleaning and drying process.

The umbilicus of newborn babies is a very tender area for about ten days following birth. Efforts have been extended to protect this area while the umbilicus is healing. However, the prior art has not disclosed a diaper which adapts to the anatomy of this unhealed navel cord while snugly fitting the rest of the infant's abdomen, avoiding leakage, while preventing avoidable rubbing and irritation.

OBJECTS OF THE INVENTION

Accordingly, one object of the invention is to produce improved leakproof undergarments for infants, toddlers, special neds children and adults of both sexes, tailored to the their anatomy and specific age level needs.

A further object of the invention is to produce leakproof undergarments that incorporate disposable or reusable fluid absorbent pads that are snugly fitted to the pubis area of a wearer without use of adhesives and plastic backing.

Another object of the invention is to produce leakproof urinals that can be used independent of, or attached and worn in, existing undergarments.

A further object of the invention is to produce a filamentary fastener of improved construction having particular utility for adjustably securing a tailored diaper to the body of a wearer.

Another object of the invention is to produce fluid absorbent, easy to clean reusable pads for diapers and the like, having superior fluid absorbing construction and improved rapid drying characteristics.

SUMMARY OF THE INVENTION

The instant invention discloses a waterproof diaper shell having inner and outer surfaces with a central elongated material sling. The upper and lower ends of the sling are attached through a pair of connecting pieces to the diaper shell, allowing the sides and body of the sling to float within the shell. The interior of the sling is provided with a channel to entrap and isolate fluid. The sling is attached to the arched connecting pieces to form an arcuate line, thereby recessing the channel within the sides of the sling, conforming the channel to tailor fit the pubis of the user. The elasticized sides of the sling fit in the crevices on either side of the pubis of a wearer.

The sides of the outer shell form leg holes, and at least a portion of the periphery of the shell at the leg holes is covered with an elastic trim to fit the legs of the wearer.

The sling preferably comprises a first place of waterproof material forming a sling underlayer and second pieces of waterproof material forming the suspended sides, or drop strips, of the sling. The underlayer and drop strips are sealed together and covered by elastic trim. In an alternative embodiment, the sling comprises a common piece of waterproof material integrally forming the underlayer and drop strips of the sling. The underlayer and drop strips are demarked by a fold line which is sealed and covered by elastic trim.

The disclosed diaper preferably includes a fluid absorbent pad insert positioned in and laterally retained by the recessed arcuate ends of the channel. The pad insert advantageously contains a fluid absorbing chemical gel material.

Other embodiments include a decorative layer of material overlying an outer surface of the diaper's waterproof shell. A transverse band of material overlying and attached to one end of the diaper shell at the sling can be incorporated to establish a waist band. This waist band preferably is attached to the sling along an arcuate line of attachment.

A device for securing a garment to the body of a wearer is also disclosed. The device comprises at least one strip of filamentary fastener material on an outer surface of the garment, and strips of complementary filamentary fastener material for attachment to the strip when the garment is worn. The complementary strips comprise a first strip of loop-type material having its center portion attached to the interior of the garment, loop side adjacent the garment. One third of the strip extends beyond the garment edge and is provided with a hook type fastener centered on the non-loop side. It is preferable that the hook-type fastener does not extend the entire length of the non-loop portion, thereby forming a hinge at one end and a pull tab at the other. The remaining third is folded over the center third, exposing the loop side and serves to secure the hook portion during washing, and the remaining portion extending beyond the garment edge. Alternatively, the loop strip can be divided into two portions. One portion is secured to the garment with its loop bearing surface adjacent to the garment. A second strip of loop-type material is attached to the portion of the first strip attached to the garment. The second strip of loop-type material is oriented with its loop bearing surface exposed. A strip of hook-type filamentary material is attached to the non-loop side of the unsecured portion of the first strip.

A fluid absorbent pad insert for use in the disclosed diaper comprises multiple layers of fluid absorbent material. The layers are secured to one another and have their surfaces freely floating. The layers of fluid absorbent material provide additional fluid evaporation surfaces to facilitate drying. Preferably, the layers are elongated in shape, and a common seal extends longitudinally or laterally. The common seal can alternatively be located at one end of the multiple layers. The layers can be staggered relative to each other along the common seal. The layers furthermore can be approximately V-shaped and have a base facing a common direction.

In another embodiment, a tailored urinal comprises a diaper shell of waterproof material with an inner liner of fluid absorbent material circumscribed by waterproof material. The peripheral edge of the shell is covered by an elastic trim, with one end arcuate in shape, bifolded and jointed to form a cusp. Preferably, one end of the shell has a waist strap to wrap around the wearer. The opposite end of the shell has an extended layer of waterproof material folded inwardly to form a cuff. The inner surface of the shell has an elastic strap to retain a pad insert.

An additional embodiment discloses a tailored urinal adapted to fit within the user's underwear. The urinal comprises an elongated, approximately rectangular diaper sling of waterproof material. The waterproof sides of the sling prevent fluid from escaping the sling. The sling has an inner liner of fluid absorbent material with a length less than that of the sling. The inner liner has a frontal end floating to receive and pocket a fluid absorbent pad insert. Alternatively, the ends of waterproof material can be folded in to receive and pocket the ends of a fluid absorbent pad insert. A fastener can be located at one end of the sling for retaining the urinal about the waist of a wearer. Alternatively, a fastener is implemented for retaining the urinal inside an undergarment. At least a portion of the peripheral edge of the sling is covered by an elastic trim.

A slip-on underwear is also disclosed which comprises an underwear garment formed of an hourglass piece of material folded and joined on opposite sides by garment waist-to-leghole seals. The underwear garment incorporates the disclosed fluid absorbing sling and can have either an elastic waist or the side fastening means.

Also disclosed is an urinal to be worn by a male. The urinal comprises a generally tubular receptacle of waterproof material with an upper end adapted for attachment within the inner surface of a garment and positioned for receiving the penis of a wearer. The wall of the tubular receptacle facing the penis is opened longitudinally to define flexible "wings" surrounding a penis entry opening. Fasteners formed on the wings retain the entry opening about the penis. Preferably, the fasteners comprise filamentary fastener strips, positioned on the receptacle to enable the strips to adjustably define the diameter of the penis entry opening. Preferably an undergarment retains the receptacle in a pocket formed on the inner surface of the undergarment, beneath the pubis of the wearer. Optionally, a fluid absorbent pad insert can be used within the receptacle. Inner edges of the wings are arc-shaped to accommodate anatomical sizing. In one embodiment, one of the wings is fixed and the other swings free.

Still other objects and advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

DETAILED DESCRIPTION OF THE INVENTION

Figures 1, 1A, 1B:
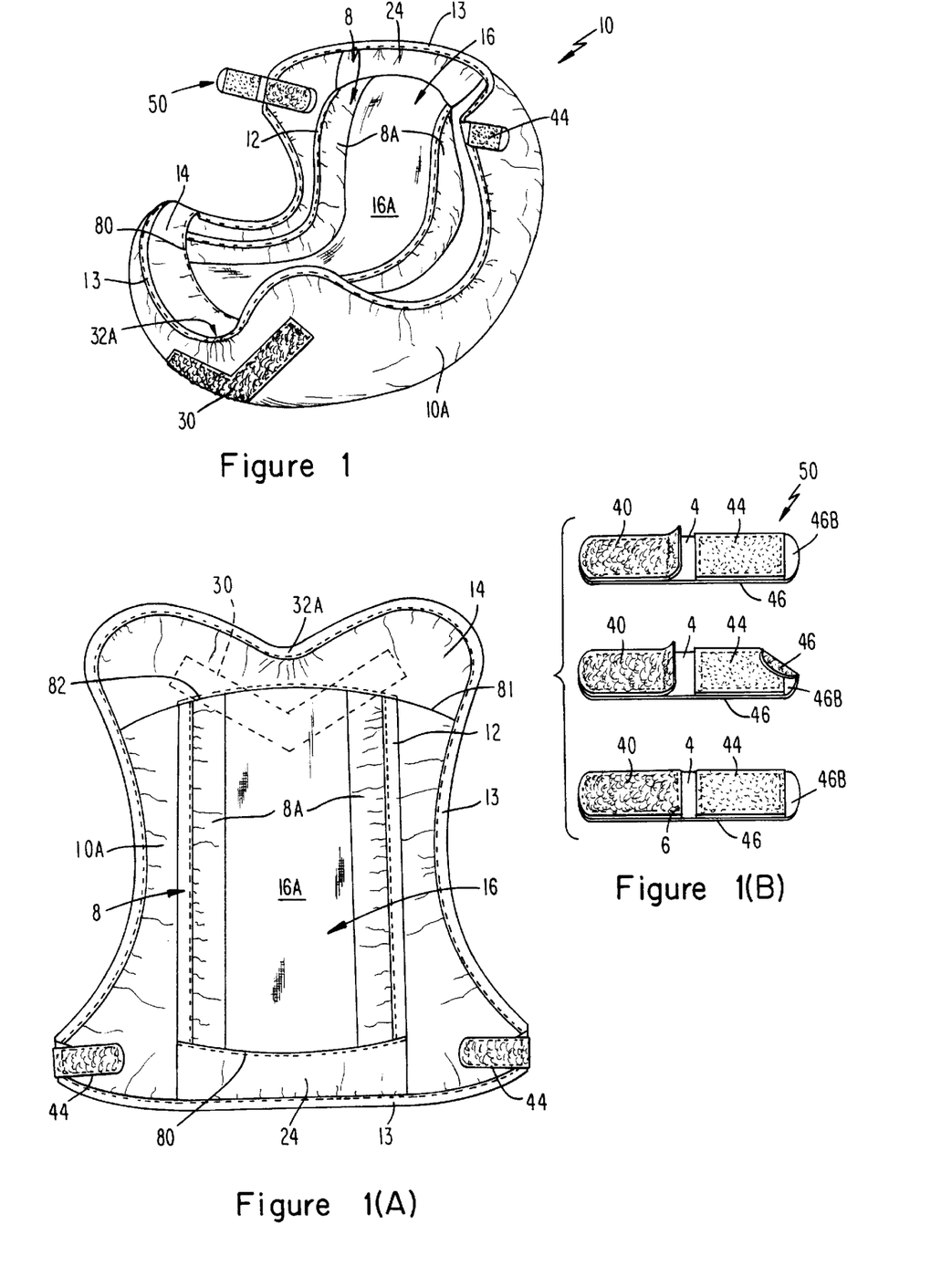
FIG. 1 is a perspective view of the disclosed reusable diaper having a waterproof diaper shell and floating sling.
FIG. 1(A) is a front view of the diaper of FIG. 1 showing the inner surface of the diaper with sling, fluid isolation barriers and adsorbent pad.
FIG. 1(B) is a front view the filamentary fastener strip disclosed in the instant invention.

FIGS. 1 and 1(A) illustrate the tailored diaper 10, in accordance with the invention. The diaper 10 comprises an outer, waterproof shell 10A, which is dimensioned to fit between the wearer's legs and be secured to itself at the wearer's waist. The diaper 10 may be hourglass-shaped, as shown, or another suitable, basically rectangular shape. A waterproof, substantially rectangular sling, or hammock, 8 is used to hold the absorbent portions of the diaper 10. The sling 8 is affixed to the waterproof shell 10A, supending it within the waterproof shell 10A hammock style. The sling 8 is secured at its back and to the waterproof arc rear bumper 24 and at its front end to the arc frontal bumper 14, thereby leaving the sides of the sling 8 floating between the leg holes of the shell 10A.

The arc rear bumper 24 is preferably the approximate width of the sling 8, once constructed, having a concave-convex configuration. The outer peripheral edge of the arc rear bumper 24 is configured to the periphery of the diaper 10 while the interior peripheral edge 80 is arcuate. The arc rear bumper 24 is affixed to the waterproof shell 10A at elastic strip 13 and to the sling 8 and drop sides 8a along the peripheral edge 80.

The waterproof, arcuate frontal bumper 14 is the width of the diaper shell 10A and conforms to the configuration of the outer periphery of the diaper 10. The arcuate frontal bumper 14, and shell 10A, have an outer peripheral edge having a concave portion 32a, at approximately the center of the shell 10A, forming a sinasoidal shape along its periphery. The elasticized concave portion 32A creates a pouch in the frontal part of diaper 10, just under the naval, which provides support for the umbilious from flat surfaces under the infant. The pouch prevents the diaper from unnecessary rubbing of the umbilicus causing irritation. The interior peripheral edge 81 of the frontal bumper 14 is in the form of an arcuate line. The frontal bumper 14 is attached to the sling 8 along the line of attachment 82.

The arc rear bumper 24 and frontal bumper 14 are joined to the shell 10A through elastic trim 13 which extends along at least a substantial portion of the periphery of the diaper 10 and helps provide the contour fit.

Along either inner side of the sling 8 are the fluid isolation drop strips 8A. The drop strips 8A are attached to the sling 8 and elasticized at the joining line through use of elastic strip 12. The drop strips 8A are seen more clearly in FIG. 4A and are described in more detail in connection with that Figure.

Within the waterproof sling 8 is an absorbent channel 16A. The channel 16A has a width less than that of the sling 8 and a length less than that of the diaper shell 10A. The channel 16A is covered with a soft, non-skid material and is disclosed in further detail in FIG. 4A. The sling 8, together with the arc rear bumper 24 and arcuate frontal bumper 14 and in combination the fluid isolation strips 8A, surround the fluid absorbent channel 16A to form the pocketed cradle 16.

The arcuate lines of attachment 80 and 82 establish a recessing and pocketing of the channel 16A and strips 8A, causing the surface of the channel 16A to become recessed within the strips 8A, the arc rear bumper 24, and the arcuate frontal bumper 14. The sling 8 encases the pubis of the wearer in a pocket. This pocketing action is enhanced by the elastic trim 12 on the edge of the sling 8 so that the entire cradle 16 will cup the pubis tightly and retain and absorb fluid. The waterproof elements surrounding the channel 16A serve to force the fluids to flow back onto the channel 16A for absorbtion. The arcuate lines are critical to the fit of the diaper. The arc shapes the cradle 16 to conform to the curve of the human body, preventing the cradle 16 from flattening. The curve of the cradle 16 additionally retains an absorbent pad 19, which is described in detail further herein. The greater the arc the greater the curvature, however too great an arc forms too deep a pocket. The deeper pocket prevents the cradle 16 from coming into contact with the pubis area and allows for leakage.

As mentioned previously, circumscribing the periphery of the diaper shell 10A is the elastic trim 13. The elastic trim 13 causes the shell 10A to embrace the pelvis, stomach, buttocks and legs while holding the cradle 16 tight against just the central pubis. Hence, the body fluids discharged from the wearer are absorbed directly into the channel 16A. The drop strips 8A, arc rear bumper 24 and frontal bumper 14 restrict the fluid from escaping the channel 16A. Any fluid that overflows the drop strips 8A becomes contained within the waterproof shell 10A and dispersed along the inner surface of the shell 10A. Any overflow fluid tends not to leak out through the leg holes or any area where elastic trim 13 conforms the outer shell 10A to the body torso.

The diaper 10 is secured to the body of the wearer by hook and loop type filamentary fastener strips, snaps or any other method known in the fastening art. For ease of discussion, only the hook and loop type fasteners will be described. The hook portion fasteners 44 project outward from each side of the rear portion of the diaper 10. The fasteners 44 are positioned to wrap around the waist of the wearer and couple to loop portion of the filamentary fastener 30 at the front portion of the outer surface of the shell 10A.

The loop portion strips 30 are arranged in a V-pattern on the front surface of the shell 10A. This pattern, together with the arcuate construction of 32A, tends to produce a pouch just above the V-pattern so as to protect the umbilious of an infant wearer. The force of the hook-type fasteners 44 pulling on the V-shaped filamentary strips 30, together with elasticized curve 32A, form a novel projecting pouch just under the infant's navel.

Referring to FIG. 1(B), the fastener strip 50 is comprised of the soft loop portion 40 ovelying tab 46, facing the inside of diaper shell 10A. The hook portion 44 on tab 46, is on the same side facing inside of the shell and is positioned to mate with the loop portion 40 during the washing process in order to protect the hook. In use, the hook portion 46b overlies a corresponding loop section 30, on the front of diaper 10. The obverse side of the hook portion 44, of the tab 46 contains loop material. Therefore, the hooks of one tab 46 can overlie the loops of the opposite tab 46, where is user is very small.

The region 4 of strip 46 is devoid of hook-type filamentary material and forms a hinge to enable the hook portion 44 to fold into contact with the loop portion 40, enabling the loop portion 40 to cover and protect the hook portion during washing. The region 4 tends to develop a "memory" which, together with the weight of hook-type filamentary region 44, causes the strip to fold during washing so that the hook 44 and loop 40 filamentary materials will mate, and the hook-type material swings on its weighted hinge 4 to cover the hook material during washing. The terminal end portion of the strip at 46b is also devoid of hook-type filamentary material to avoid discomfort to the wearer as the end of the strip presses against the thumb when opening the tab and can hurt the skin of the thumb.

Figure 2:
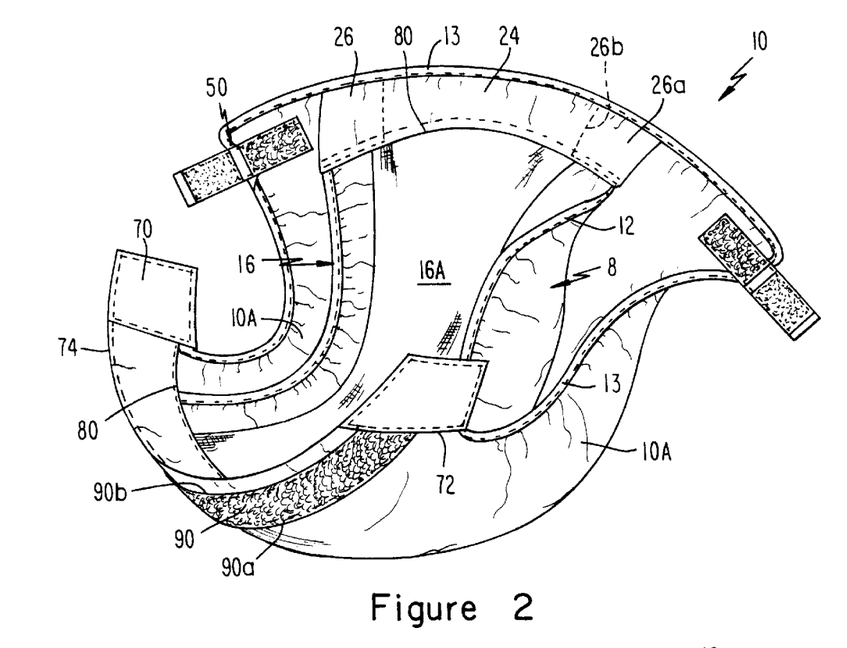
FIG. 2 is a perspective view of another embodiment of the reusable diaper of the instant disclosure.
Figure 2A:
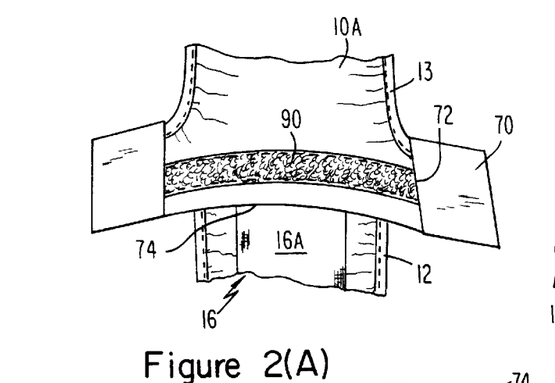
FIG. 2(A) is a top view of the unfolded protective wing construction of FIG. 2.
Figure 2B:
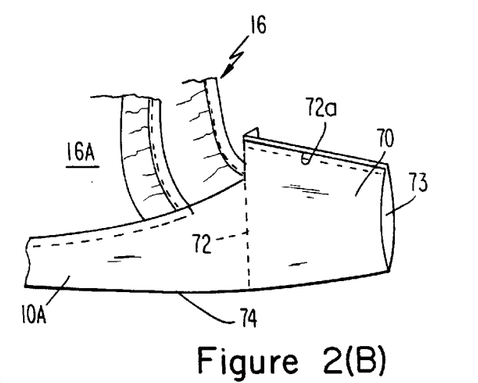
FIG. 2(B) is a front view of the folded protective wing construction of FIG. 2A.
Figure 2C:
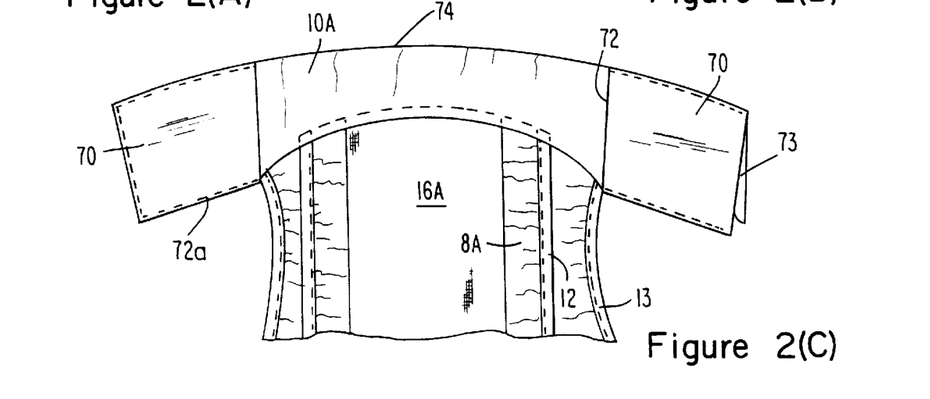
FIG. 2(C) is a front view of the folded and stitched wing construction of FIG. 2.

A second embodiment of a diaper, or diaper cover, is shown in FIGS. 2, 2A, 2B and 2C, utilizing a basic construction similar to that of FIG. 1. The loop-type fastening bar 90, on the front of the diaper extends along the entire width of the waterproof shell 10A with the ends hidden by protective wings 70. Assembly is made by joining fastening bar 90 along the edges 90a and 90b before folding the shell 10A inward or attaching wing 70. The wings 70 are attached at joining line 72, sealing the ends of bar 90 as shown in FIG. 2A. The shell 10A is folded at fold line 74, extending the full frontal width of the shell 10A, and the channel 16A is turned to the outer back side of diaper 10 so as to join the wings 70 to each other on line 72a. The channel 16A is flipped to inside of garment and the wings 70 are turned right side out leaving only the most exterior end 73 open for sealing of the finished garment. The ends 73 may be finished off either by folding them inward and top stitching or in another sewing or sealing method. Alternatively, the fastening bar 90 is initially secured to the shell 10A only along line 90a. The protective wings 70 are secured to the shell 10A along line 72, thereby encasing the ends of the fastening bar 90 between the shell 10A and the protective wings 70 and eliminating the need to finish the raw ends of the fastening bar 90. The shell 10A is folded at fold line 74, finished sides adjacent, and stitched along line 72a. The shell 10A is then turned right side out, thereby exposing the finished sides. The fastening bar 90 is further secured by affixing the fastening bar 90 and both layers of outer shell 10A together along line 90b. This is generally accomplished by top stitching, although other methods can be used dependent upon the material of manufacture.

Another novel feature of FIG. 2 is in the rear bumper strip 91. The bumper strip 91 is joined to the shell 10A along an arcuate line 80 to produce the pocketing and recessing of the channel 16A as disclosed heretofore in connection with the arc rear bumper 24. The bumper strip 91 has width greater than that of the sling 8 allowing for fold-under tabs 91a and 91b. The fold-under tabs 91a and 91b are folded under and joined at lines 26b. The bumper strip 91 provides additional strength to the assembly, avoiding tearing during multiple uses and washings.

Figure 3:
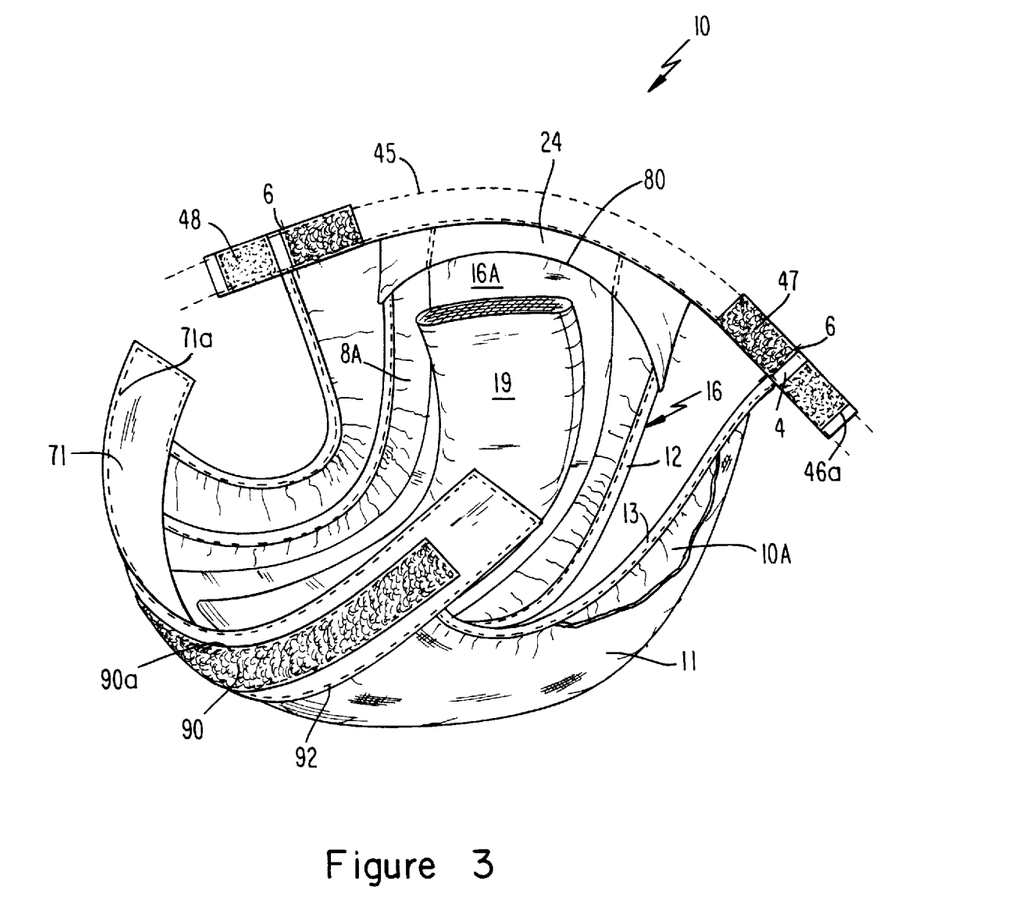
FIG. 3 is a perspective view of an alternative embodiment of the instant invention.

Referring now to FIG. 3 it is illustrated how the recessed cradle 16 accommodates an additional absorbing pad insert 19. The pad insert 19 is maintained in position due to the boarding recessed structures. The drop strips 8A prevent any side to side shifting while the arc rear bumper 24 and arcuate belly band 71 prevent front to back movement. The arcuate belly band 71 works to recess the frontal end of the sling 8 and channel 16A in same fashion as arc frontal bumper 14 of FIG. 1 and folded end of diaper shell 10A of FIG. 2. The cradle 16 of all embodiments disclosed herein conveniently receive any of the pad inserts disclosed herein. The pad inserts fit the snugly within the cradle 16 because of the heretofore disclosed pocketing action. Additional security is achieved through the fabric-to-fabric contact between the pad insert 19 and the surface of the channel 16A. As stated heretofore, the surface of the channel 16A is preferably manufactured from a soft, absorbent material. The pad insert 19 can be either a disposable pad, such as known in the sanitary napkin industry, or a reusable pad, as disclosed further herein. The two materials serve to present substantial surface friction and minimizes shifting of the pad insert 19.

FIG. 3 also illustrates a decorative fabric outer layer 11 over the surface of diaper shell 10A. The decorative fabric outer layer 11 can be a non-waterproof material and allows for a greater variety of designs. The belly band 71 can be used with the decorative outer layer 11 and is attached to the stomach portion of the diaper 10, carrying the loop-type fastener strip 90. The belly band 71 extends beyond the shell 10A on either side and encases the diaper shell 10A, sling 8 and channel 16A. The belly bend 71 can be two pieces of fabric or one piece folded prior to securing at line 71a. To prevent leakage, the fastener strip 90 is only attached to the front portion of the belly band 71, preventing penetration of the underlying waterproof fabric at either join line 92 or sealing line 90a. The cradle 16 is attached to the interior of the belly band 71 as described heretofore and provides the same pocketing action.

By extending the belly band 71, or wings 70, beyond the shell 10A, a soft, protective barrier is formed. This protective barrier is also achieved in FIG. 1 through placement of the fastening means. In order to secure the diaper 10, the fastening means must be placed a distance from the periphery of the diaper adjacent the fastening means. This insures that once fastened there is fabric between the fastener and the wearer's skin. This is most obvious with the use of hook and loop type fasteners where the hook portion can be irritating when in contact with the wearer's skin for any period of time. In infants and small children, this is of a concern as they are generally not able to isolate the irritation. By placing all fastener strip disclosed herein a sufficient distance from the periphery of the diaper 10, contact between the skin and the fasteners is avoided.

Figures 4, 4A:
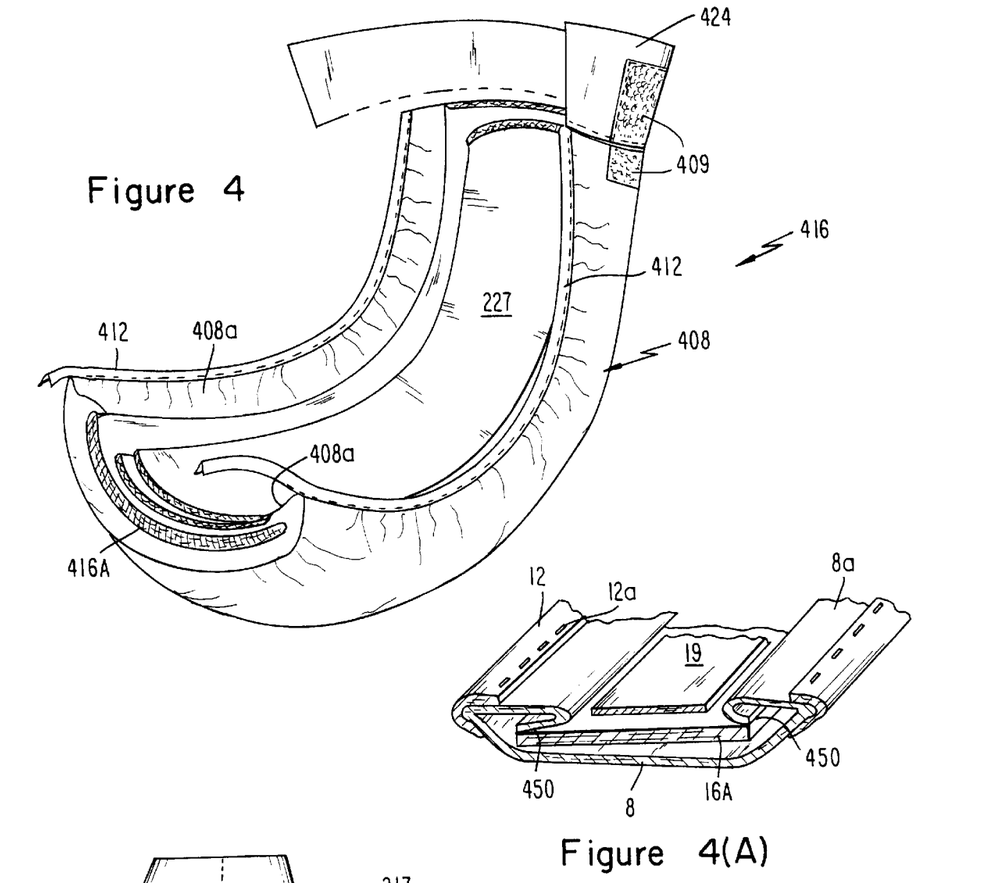
FIG. 4 is a perspective view of a novel fluid absorbent diaper, adapted to be worn within underwear.
FIG. 4(A) is a perspective end view of the absorbent channel of the instant disclosure.

The details of the cradle 416 construction are illustrated in FIG. 4, wherein the cradle 416 has been separated from the diaper shell 410A. It is clearly illustrated how the sling 408 forms and supports the exterior side of the cradle 416. The drop strips 408a are stitched to the channel 416a and placed within the sling 408. The strips 408a and sling 408 are secured together and elasticized with elastic 412, thereby forming the contoured cradle 416. The elastic 412 can be any method for elasticizing, such as fabric encased elastic or standard elastic strips, which are stitched on. If used as a disposable, the elastic can be heat generated as well known in the disposable diaper art. The open ends of the cradle 416 are affixed, along an arcuate line, to the arc rear bumper 424 and the frontal bumper 414 (not shown) as previously described.

The cradle 416 of FIG. 4 can be utilized with undergarments which have had an additional piece of loop-type material added. The loop-type material is added to the front and back of underwear to approximately match the width of the channel 416. The hoop-type material 409 has been added to the exterior of the sling 408, the arc rear bumper 424 and the frontal bumper 414 (not shown). The cradle 416 can them easily be incorporated in standard underwear and removed for washing.

The removability aspect of the cradle 416 can also be incorporated in the disclosed diaper shell 410A. A reaffixable fastening means 409 is affixed to the exterior side of the sling 408, the arc rear bumper 424 and the frontal bumper 414 (not shown). The diaper shell 410 would be assembled with the the arc rear bumper 24 and the frontal bumper 14 as previously disclosed, however the cradle 416 would not be affixed thereto. The the arc rear bumper 24 and the frontal bumper 14 are provided with the mating portion of the fastening means affixed to the exterior of the frontal and rear bumper 424 and 414 and the sling 408. The the arc rear bumper 424 and the frontal bumper 414 are provided with finished edges and are placed over the mating portion. The fastening means 409 can be a hook and loop filamentary fastener strip or other means will provide the desired result. Other methods of assembly can be provided to accomplish the removability of the cradle 416, however it the arcuate lines described herein must be maintained in order to have the desired pocketing affect.

The internal construction of the channel 16A is illustrated in FIG. 4(A). The drop strips 8a and sling 8 as illustrated in this embodiment are one piece of material which is folded and held in place by elastic trim 12. The elastic trim can be a fabric encased elastic which is stitched along stitch lines 12a on either side of the fold. The drop strips 8A and sling 8 can alternatively be two separate pieces of material which are secured together by being encased in the elastic trim 12. The drop strips 8a are affixed to the periphery of the channel 16a, along sealing lines 450, thereby forming the hammock affect. The suspension of the channel 16A by the drop strips 8a enables the channel 16A to shift laterally. The ability to shift laterally allows the channel 16A to maintain contact with the pubis, containing and restricting the flow of fluid, during movement of the wearer. It is a critical aspect of the invention that the channel 16A have the ability to float within the sling 8 structure. That is, the channel 16A is free to move laterally relative to the elastic 13 which is maintained in a fixed position on the wearer's legs. Thus, the position of channel 16A stays constant relative to the pubis, since it is independent of movement of the remainder of the sling. Some materials may require further definition at the fold lines, an option which can be accomplished through pressing, heat sealing, or other methods known in the prior art. The removable pad insert 19, is shown in its position relative to the other elements of the channel 16A. The disposable and non-disposable removable pads are disclosed in more detail herein, all of which are interchangeable in the diapers disclosed herein.

The channel 16A can be manufactured either from a soft absorbent or non-absorbent material having a non-skid surface. An absorbent polyester material with a top covering of either flannel, cotton or other absorbent material is an example of an absorbent combination. A non-absorbent material, such as used in infant lap pads, can be used as it holds it shape and has a soft, non-skid surface. A non-absorbent material would be used in combination with a disposable or non-disposable absorbent pad.

Figure 5:
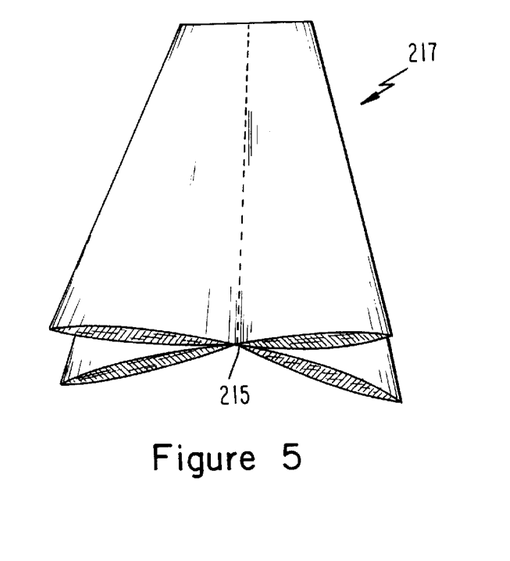
FIGS. 5 is a perspective view of the non-disposable pad of the instant invention.

FIG. 5 depicts a non-disposable absorbent pad 217, adapted to be seated in the cradle 16 as disclosed herein. The absorbent pad 217 has a novel, multi-layered, butterfly construction. This butterfly construction is formed of two elongated pad layers, bisected longitudinally by a joining line 215. The bisection creates a pad of eight effective evaporation surfaces, each spanning the length of the pad and one-half its width. The resulting pad is thin but will dry more rapidly than a single layer pad. The non-disposable absorbent pad 217 provides extra absorbency while still protecting the environment. The absorbent pad 217 can easily be removed and washed. The absorbent pad 217 is manufactured from an absorbent material and covered with a non-skid material. The non-skid material of the absorbent pad 217 works in combination with the pocketing configuration of the cradle 16 and the non-skid material of the channel 16A, to hold the absorbent pad 217 in place. The absorbent pad 217 can be used for total absorption, thereby eliminating the need to change the diaper 10 after each elimination. The absorbent pad 217 is replaced and the diaper 10 changed once or twice each day.

Figure 5A:
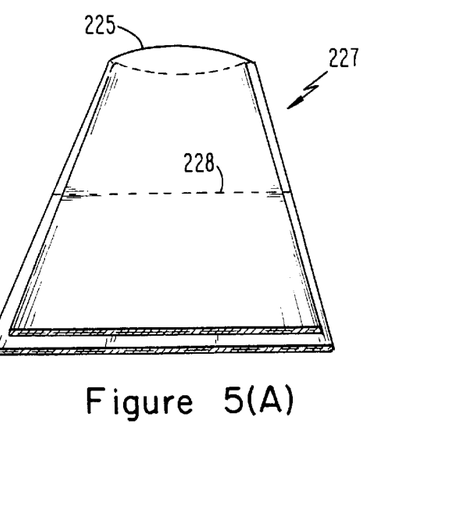
FIG. 5(A) is perspective view of an additional embodiment of the non-disposable absorbent pad of FIG. 5.

An alternate embodiment to the absorbent pad 217 is shown as pad 227 in FIG. 5A. The dividing line in the pad 227 is a transverse stitch line 228. Preferably the outer layer is slightly larger than the inner layer to eliminate bulk. The pad 227 is shown in FIG. 4 placed in the cradle 16. It can be seen in FIG. 4 how the pocketing of the channel 16A holds the pad 227 in place without shifting. One end of the pad 227 is illustrated cut in an arc 225 to facilitate insertion into the arc rear bumper 24 disclosed herein. One or both ends of any of the disclosed pads can be arched to conform to the arcuate lines of the channels 16A. The layers of the pads can alternatively be stitched together at one end or side to present additional evaporation surfaces.

Figures 6, 6A, 7, 7A:
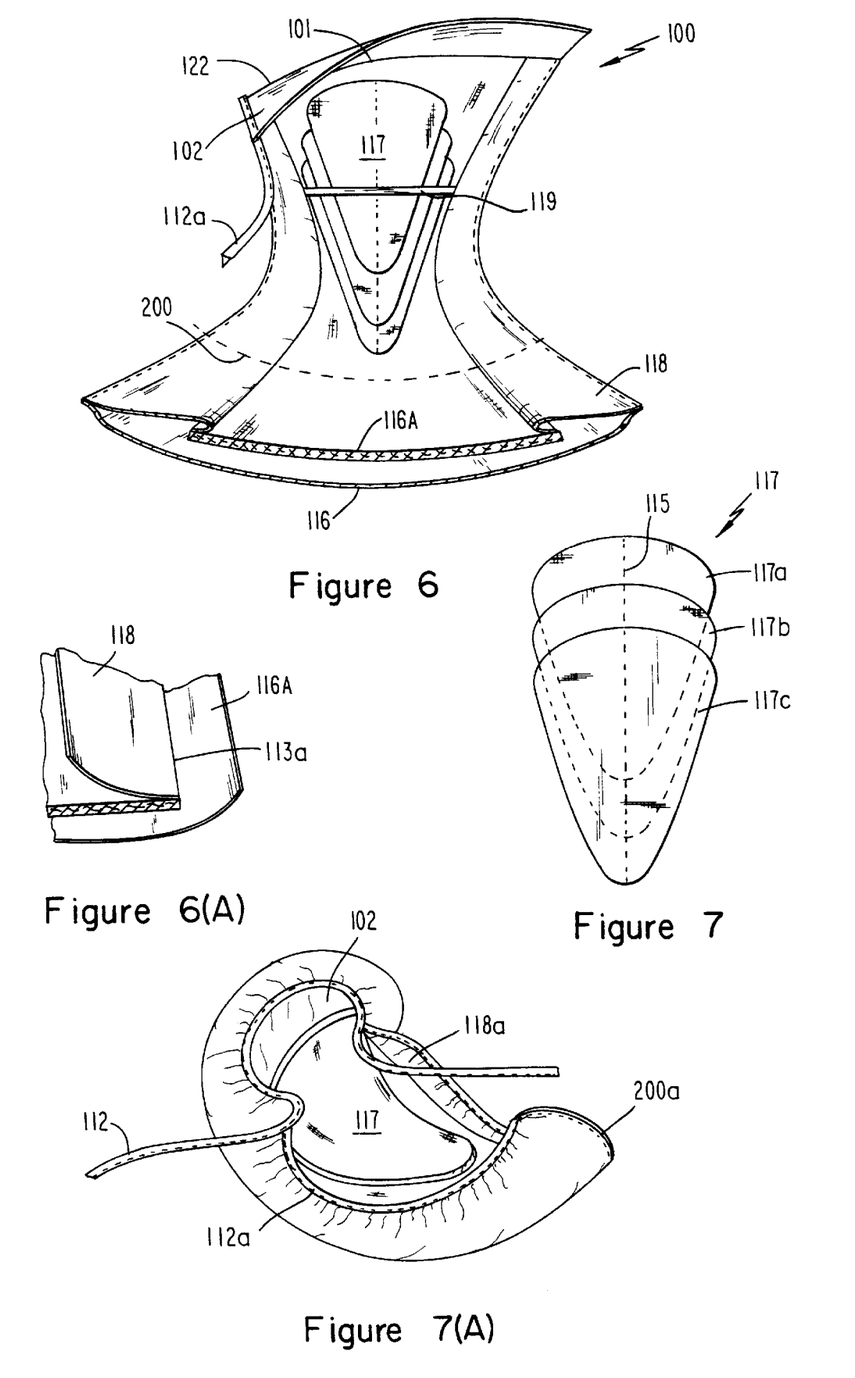
FIG. 6 is a perspective view of the fabric urinal of the invention, in an intermediate state of construction.
FIG. 6(A) is a cut-away perspective view of the fabrication of the urinal of FIG. 6.
FIG. 7 is a top view of the disclosed V-shaped absorbent pad utilized in the urinal of FIG. 6.
FIG. 7(A) is a perspective view of the urinal of FIG. 6 in a final stage of construction.

Referring now to FIG. 6, a novel channel structure of this invention is implemented in an adult garment or extra large child size garment. The configuration of the cradle indicated generally as 100, is of hourglass-shape. The drop-strips 118 can be separate elements, rather than folded, beneath the elastic trim 112a. As seen in FIG. 6, the process of applying elastic 112A to the edges actually pulls the end of channel into a natural arc 122 for fitting to an arc bumper to be attached to an adult size under garment (not shown).

The channel member 116A and the under-surface material 116, are also of hourglass configuration to conform to the shape of the adult size garment. The internal construction of the channel 116A is the same as in FIG. 4(A) of the previously disclosed embodiment, except waterproof material under-surface material 116 can be extended to line 101 and folded inward to form a cuff 102, as best shown in FIG. 7(A). The channel 116A, accordingly, is able to shift laterally by virtue of being suspended by the drop strips 118, while remaining relatively fixed in the longitudinal direction, by being attached at its opposite ends. A V-shaped pad insert 117, having the "butterfly" multiple layered construction, is positioned in the region of the channel member 116A, beneath the elastic strips 119. The V-shaped pad insert 117, shown in greater detail in FIG. 7, comprises multiple layers 117A, 117B, and 117C, aligned laterally and staggered longitudinally. The multiple layers can be sealed to each other centrally, along line 115, by any convenient means, preferably, by being sewn together.

Another aspect of the invention, shown in FIG. 7(A), a fabric urinal for bedridden patients is formed by cutting along the arcuate line 200 in FIG. 6, and sealing the now exposed edge together to establish the receptacle shown in FIG. 7(A). the joined end 200a is positioned between the legs of the wearer. The optional elastic strap 112 can be wrap around the waist of the user for additional stability. The elastic strap 112 is preferably, sewn to the cradle 100, along the fold line 100, of the cuff 102, that is, along the peripheral edge of the cuff 102. Within the urinal shown is located the absorbent pad insert 117 of FIG. 7, conveniently removable for launder and reuse. Alternatively, the pad 117 of FIG. 7 can be replaced by a disposable gel-filled pad of similar V- or teardrop shape. It should be understood that the term "gel-filled", as used in this specification, is intended to mean super-absorbents, as well known in the art. The urinal can be folded flat, slipped under the patient and opened to cup the pubis, a novel process considerably more convenient, efficient and comfortable than conventional hospital bed pans.

Figure 8:
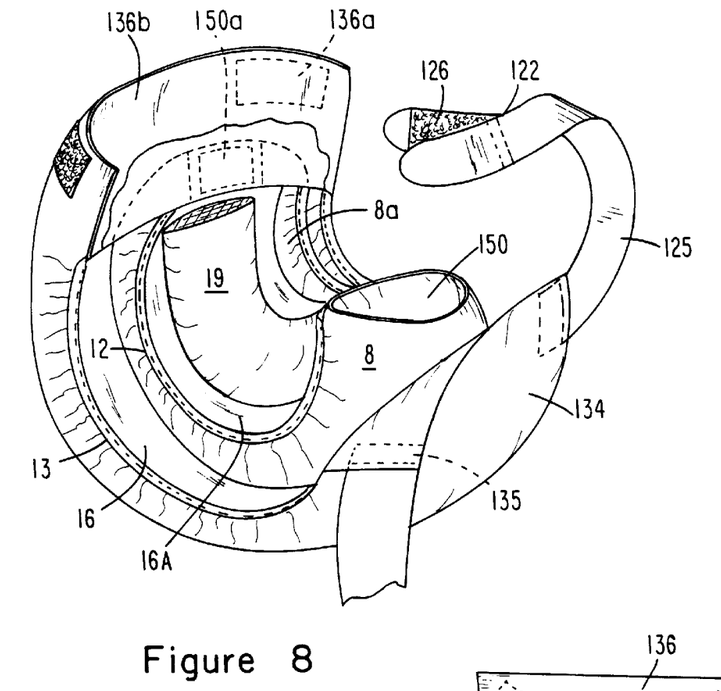
FIG. 8 is a perspective view of an urinal of cuffed construction, adapted to be worn within underwear.

The embodiment of FIG. 8 shows an undergarment indicated generally as 134, with a detachable cradle construction, the details of which have been described in connection with FIG. 4. FIG. 8 shows is a mechanism for closing the ends of the channel 16A. A fastening means 150 adapts for attachment to garment shell 134, at the central inner surface of the underside of cuff 136b. The corresponding attachment means 150a, on underside of cuff, can be a hook filamentary fastener for the underside placement would protect it from destruction in the wash. In this instance, the fastening means 150 would be a corresponding loop fastening member which needs no cover during the the wash step. The closings of the ends of sling 8 form pockets for receiving an additional fluid absorbent pad insert 19 as shown. There will be no slippage as a result of fabric-to-fabric contact in addition to the closed ends of the cradle 16.

Figure 8A:
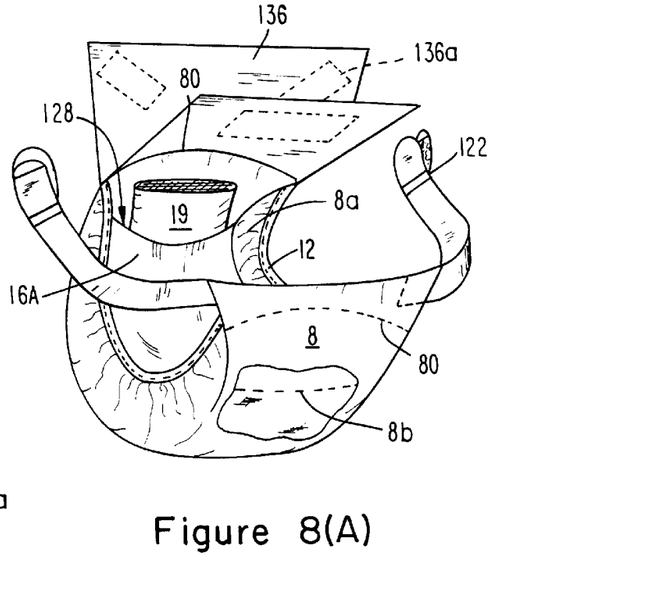
FIG. 8(A) is a perspective view of a modification of the embodiment of FIG. 8, having waist belt pad pocket.
Figure 8B:
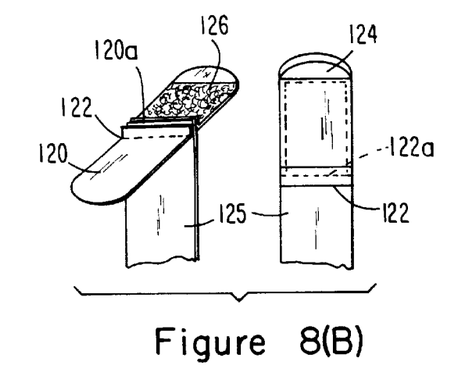
FIG. 8(B) illustrates construction details of the filamentary fastener strips of the instant invention.

In FIGS. 8 through 8(B), the outer waterproof garment shell 134 is shown with a belt 125. Preferably, the belt 125 is formed of an elastic material having loop filamentary fastener strips 120 and hook fastener 126 sealed at 122 to be mated for closure and opening at pull tab 124. The belt 125 wraps around the waist of the wearer and the hook faster 126 couples to a complementary filamentary strip 136a on the stomach portion of the shell. The belt 125 receives reinforcement sealing under the folded backband at the rear end of garment 134 at sealing lines 135.

The fastener strips at the end of the belt 125 can be of the novel construction shown in FIG. 8(B), with strips of hook and loop type filamentary material applied on opposite sides of the belt 125 and enclosing the raw end of the belt between the complementary fasteners. All three raw ends, the raw end of loop 120, the raw end of belt 125, and the raw loop end of 120a, are stitched at line 122. Hook 126 is positioned centrally and fastened to tab 120a (the back side of tab 120a), which will also become the inside of the tab when closed. Hook material 126, now fastened securely to 120a by either sealing or sewing, is ready for closure and hiding of the raw ends; however an additional joining or stitch line 122a are necessary to encase the raw ends permanently.

FIG. 8(A) depicts what is referred to herein as a double sling, with both waterproof materials 8 and 8b encased in elastic trim 12 just as other embodiments of same rectangular shaped cradle. However, the channel 16a is not sealed at arcuate line 80; instead it is left open at pocket 128 for receiving a pad insert 19. The purpose of the double sling is to allow for the tailoring of the inside sling without leakage, if sewn. Hence the pocket 128 can be sealed at the stitch line 8b and is covered by waterproof fabric 8. The same is true for the opposite end, that is, arcuate line 80, if sewn, will not leak because of the unpierced fabric outer shell 8 just behind it. FIG. 8(A) has same suggested fastening means as FIG. 8.

Figures 9, 9A:
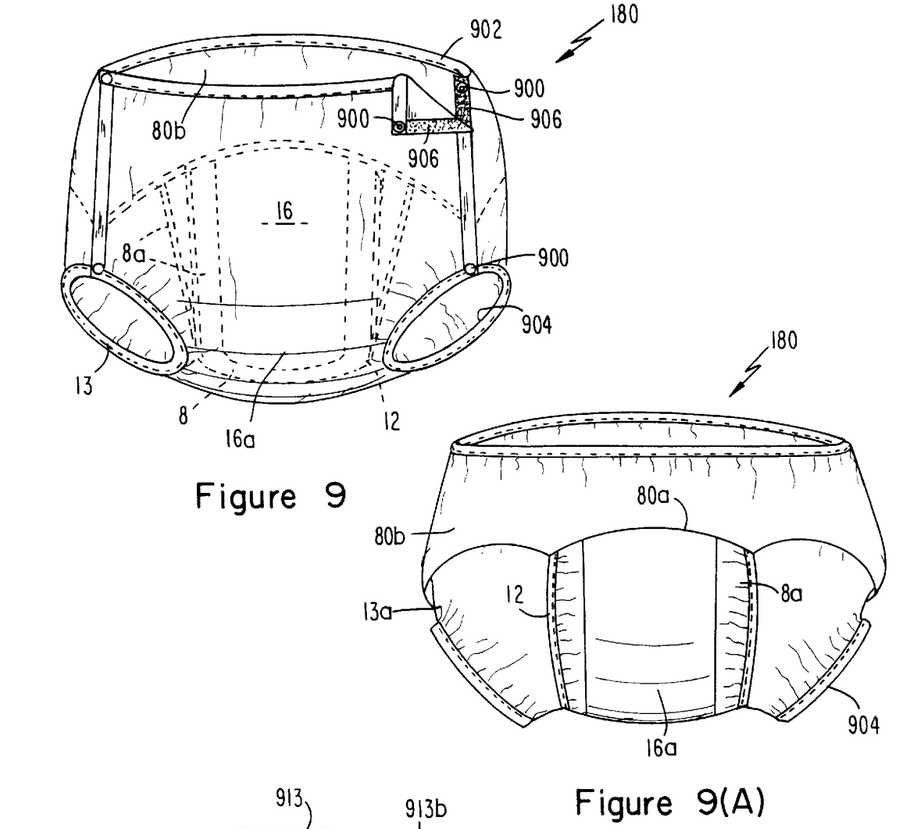
FIG. 9 is a cut-away front view of an alternate embodiment of thee diaper of the instant invention retaining an absorbent pad and adapted to be worn within, but separate from, underwear.
FIG. 9(A) is a front view of underwear containing an integral sling for separating fluid from the leg holes.

Referring now to FIGS. 9 and 9(A), the rectangular cradle of FIG. 4 and the hourglass cradle of FIG. 6 are adapted to be inserted inside a pull-up pantie or side-fastened pantie which can be pulled down or unfastened to be removed. In FIG. 9, fabric pantie 180 with the "right" side of the fabric outward, a side fastening means is adapted with snaps 900, at the waist 902, and at the leg hole 904. Complimentary filamentary hook and loop fastener strips 906 are provided in-between the snaps 900. The combination of filamentary fastener strips, supplemented by snaps (snap-tape, etc.) for strength, is novel for such panties. The combination overcomes the problem associated with hook and loop fasteners of low peal strength at the ends of the hook and loop fasteners. Thus, the snaps provide the resistance to the initiation of the opening of the securing member. The hook and loop provide the required high shear strength, that is, resistance to being pulled open. Other fastening means such as zippers, snaps etc. can be substituted, or the fastening on side can be removed in favor of a sealed or sewn joining line 13a as shown in FIG. 9(A). It is also possible to fasten only one side of the garment, such as seen in skirts etc. for easy removal.

The arcuate liner 80b, as shown in FIG. 9, and as best seen in FIG. 9(A), suspends the cradle 16 for free floating, so that the function of the leg holes 904, can be limited to fitting the legs of the wearer. The channel member of FIGS. 4 and 6 (depending on whether a toddler or adult, respectively, is being accommodated) is suspended by arc-liner 80b forming cradles for channel member 16a to fit snugly against the pubis.

All the same principles of design in this disclosure that are novel are applied to the pull-up pantie as seen in the case with all previously disclosed embodiments. The fabric for the panties of the pull-up design should be waterproof, but also can be of the stretch type, as for example, water-resistant lycra, coated polyester, Gortex, etc. Decorative materials can be added as desired. The stretch quality of fabric is not essential, but is recommended for snug overall fit of channel against the body. It should be remembered that hook and loop fastening of previous embodiments would give a circumferential fit, and pull ups rely on stretch fabric to accomplish that goal with more satisfaction to the wearer.

Figure 9B:
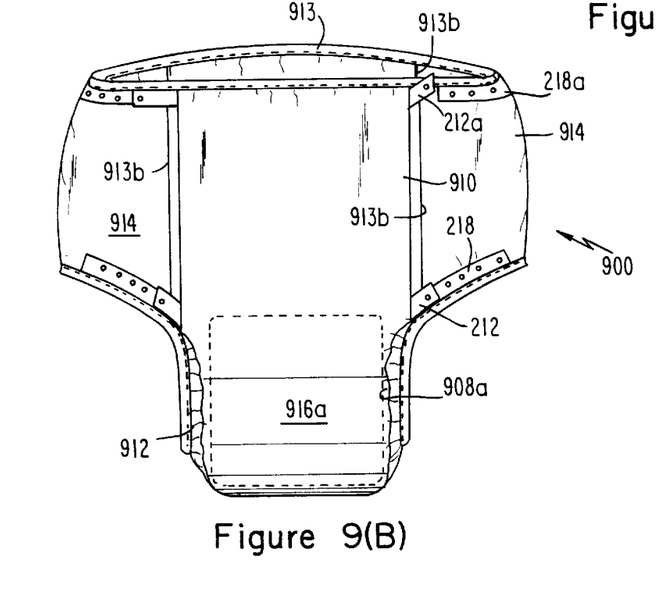
FIG. 9(B) is a front view of an alternate embodiment of FIG. 9A.

In the embodiment of FIG. 9B, the cradle 910, is constructed like the cradle 8 of FIGS. 1, 2, 3, 4, 8, 9, and 9A, but it is not attached to arcuate bumpers or liners. The cradle material 910, is extended to the waist elastic trim 913. The pad insert 916a absorbs sufficiently for light incontinence needs, is recessed by waterproof sides panels 908a and encased by the elastic material 912. The sides panels 914, of the stretch material of the pantie 900, join at four seams 913b. The fit of the pantie 900, at the waist and leg holes is adjusted by adjustment strips 212a, 218a, 212 and 218, respectively. As shown, snap tape can be used, but fastening can be implemented in other forms, such as filamentary fastener strips, as previously described.

Alternatively, the adjustment strips 21a can be secured in seam 913b in order to provide a more finished and functional process adjusting the pantie to a smaller size.

Figure 10:
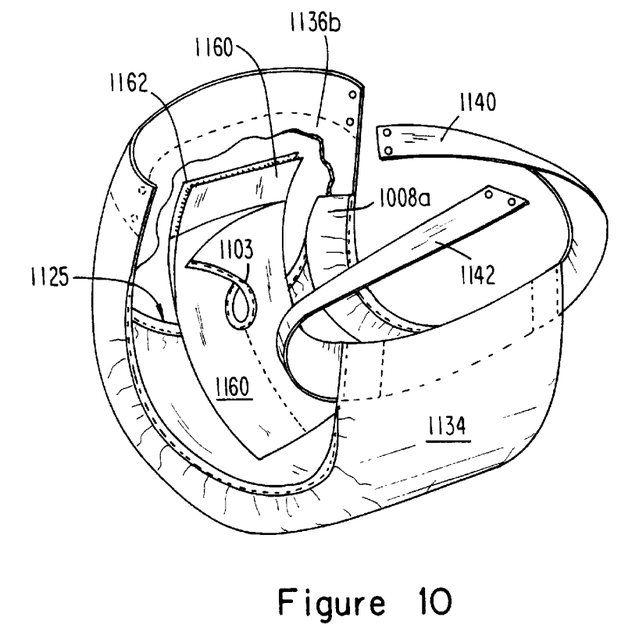
FIG. 10 is a perspective view of a fabric urinal designed to be worn by men.
Figures 11, 11A, 11B:
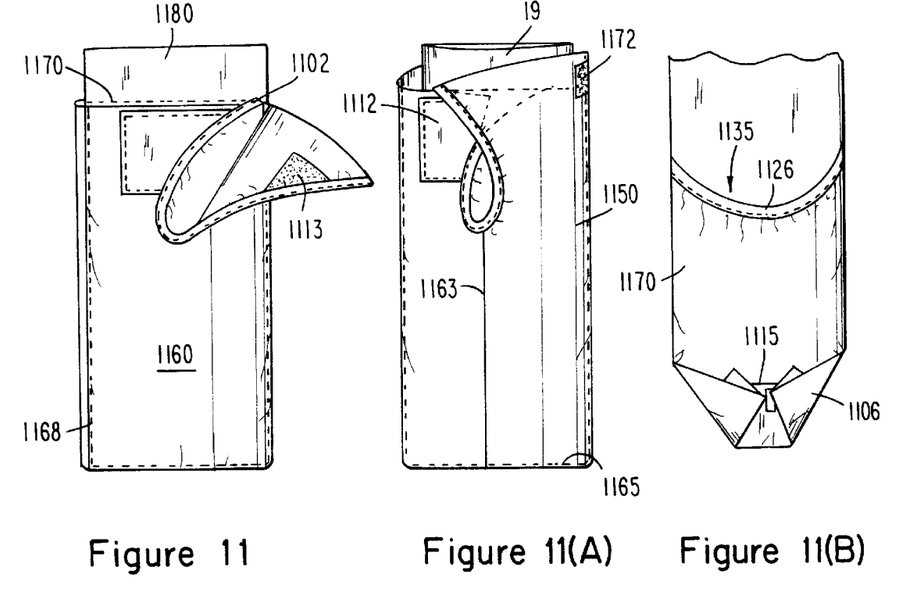
FIG. 11 is detail showing the construction of the fluid retaining receptacle of FIG. 10.
FIG. 11(A) shows the "arc-wing" construction of the receptacle for adjusting the size of the penis entry opening.
FIG. 11(B) shows the construction of the receptacle pocket retained within the shell of FIG. 10.

Referring now to FIG. 10, a modification of the undergarment of FIG. 8, can be used to accommodate a urinal for males. The basic channel structure of this invention can be used to accommodate the urinal. The urinal comprises a waterproof shell 1134, pocketed at 1125, and establishing a channel as in the previously described embodiments. At one end of the shell 1134 is a cuff 1136b for retaining, with filamentary fasteners or other suitable fastening means, one end of a novel male bag or receptacle 1160. The receptacle is tubular in shape to receive the penis, or the penis and scrotum. The receptacle 1160 has its lower end folded at 1106 as shown in FIG. 11(B). The folded corners can be secured by stitching, or advantageously, by means of hook and loop fasteners 1115, as described herein. The receptacle 1160 can be secured to the cuff 1136b by means of hook and loop connectors, where one member 1160 is secured to the inner surface of the cuff 1136b, and the reciprocal member 1162 is secured to the upper end of the receptacle 1160. In the embodiment of FIG. 11, the receptacle 1160 is formed from fabric which is folded at it lower edge and stitched along two sides by stitches 1168 and at its upper edge by stitches 1170. The upper flap 1180 can be provided with a hook or loop fastener as explained in regards to the embodiment of FIG. 10. Alternatively, the receptacle 1160 can be formed into a tube by means of a central seam 1163 and a bottom stitch line 1165. Securing of the receptacle 1160 to the cradle can be achieved through the use of hook and loop filament system as previously, described, on portion of which is shown in FIG. 11(A) as 1172.

At the upper end of the receptacle 1160, the receptacle wall is separated longitudinally and trimmed with elastic 1102, as shown in FIG. 11, with its upper ends having an arcuate configuration, and adapted to swing together and close around the stem of the penis. The outer wing of this structure is fitted internally by a strip of filamentary fastener material 1113 positioned to attached to complementary filamentary material 1112 on the underlying portion of the receptacle 1160. By adjusting the position at which the two strips of the filamentary material attach, the receptacle can adapt to males of varying size.

Preferably, the receptacle will receive a pad insert of fluid absorbent material, preferably of the super-absorbent filled variety, which can be removed following use and replaced.

As an alternative, the receptacle 1160 can be non-releasably secured to the shell 1134. In another alternative it is removable and disposable.

Formed within the inner surface of the shell is another pocket 1125, having an elastic opening, to receive and position the receptacle 1160 after the penis is inserted.

The folding of the receptacle 1160 at 1106 as shown in FIG. 11(B) eliminates the need for seam sealing the bag to prevent leakage. Any leakage, however, will be retained by the pocket 1125 within the shell 1134.

As shown in FIG. 11(B), a receptacle 1170 is provided, which has a pocket, shown as 1135. An elastic trim 1126 provides for the securing of the pocket against the stem of the penis, or the penis and scrotum.

Figure 12A:
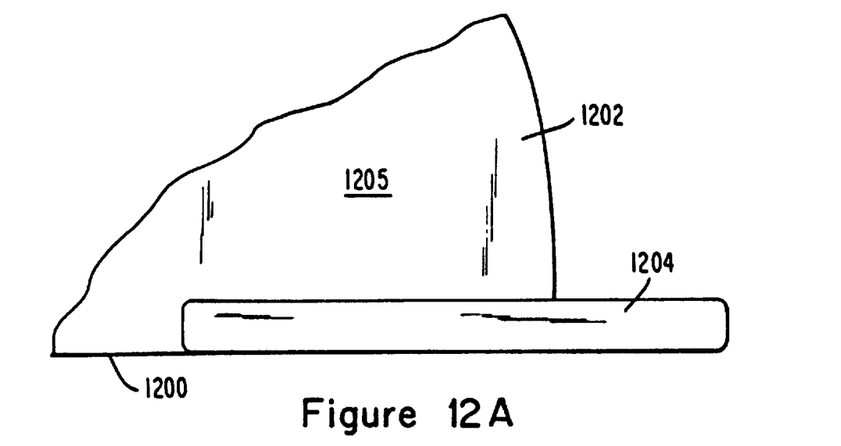
FIG. 12A is a top view of an alternate fastening means of the instant disclosure in the first stage of assembly.
Figure 12B:
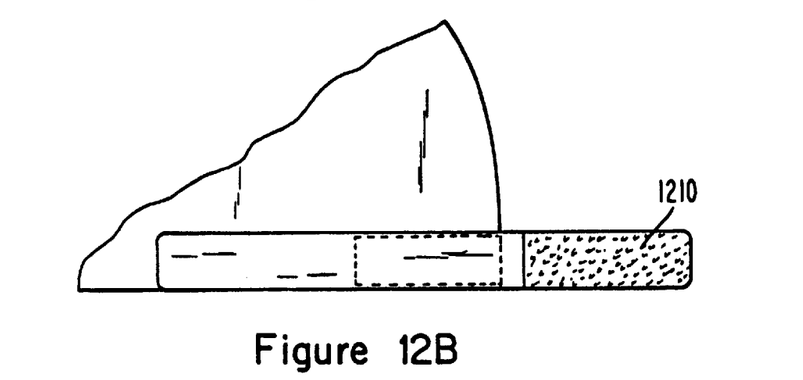
FIG. 12B is a top view of an alternate fastening means of FIG. 12A in the second stage of assembly.
Figure 12C:
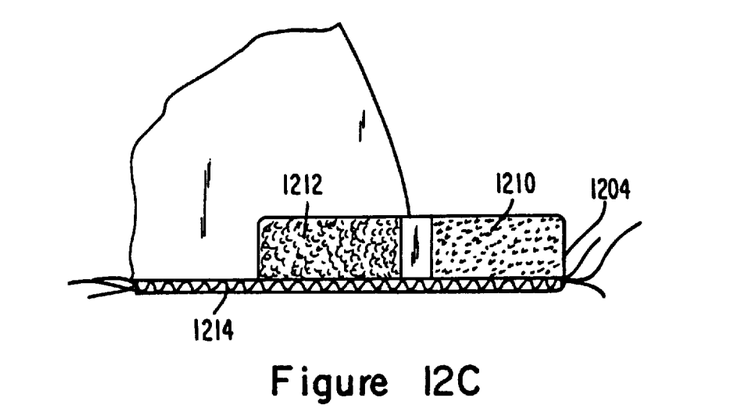
FIG. 12C is a top view of an alternate fastening means of FIG. 12A in the third stage of assembly.

The embodiment of FIGS. 12A through 12C, illustrate an alternate embodiment, relative to the fastening means of FIG. 1B. As shown in FIG. 12, a length of loop material is positioned along the peripheral edge 1200 of the shell 1202. FIG. 12 shows the facing side of the shell with a first portion 1206, of the filamentary loop material 1204 positioned against the obverse side with the filamentary loops in contact with the obverse side and a second portion 1208 exposed when the face of the shell 1202 is being viewed, as in FIG. 12. FIG. 12A shows the reverse view, relative to FIG. 12, in that the obverse side, or inside of the shell 1202 is being viewed. It is noted that the filamentary loop material is placed against the shell in the reverse manner from that which customary, in that in typical applications, the filamentary loops are exposed rather than against the fabric to which it is being attached. As shown in FIG. 12B, a length of loop material is secured to the second portion 1208 of the length of loop material 1204. As shown in FIG. 12C, about half of the first section 1206 is folded over such that the fold section 1212 of the first section 1206, of loop material 1204, has its loops facing in the same direction as the hooks of the hook section 1210. In this embodiment, a single stitch line 1214 can be run from one end of the length of loop material 1204 and overlying hook material 1210, across the peripheral edge 1200 of the shell 1202, to the opposite end of the shell 1202 and to the end of the loop material (not shown), at the opposite end, corresponding to loop material 1204.

In this disclosure, there is shown and described only the preferred embodiment of the invention, but, as aforementioned, it is to be understood that the invention is capable of use in various other combinations and environments and is capable of changes or modifications within the scope of the inventive concept as expressed herein.

I claim:

1. A urine retaining garment comprising:
    an elongated inner piece of fluid absorbent material establishing an inner surface channel for receiving a fluid absorbent pad, opposite sides of the inner piece of fluid absorbent material being profiled to conform to a user's legs; and
    drop strips of fluid resistant material extending from opposite sides of said inner piece, each strip having one side fastened to the inner piece of fluid absorbent material and an opposite side being elastic, the elastic bowing the drop strips and inner piece of fluid absorbent material longitudinally to form a cradle for cupping the pubis of the user when the urinal is worn, and wherein corresponding ends of said drop strips are joined together by an outer piece of fluid resistant material;
    a frontal end of said outer piece of fluid resistant material being inwardly folded to overly a portion of the inner surface of the inner piece of fluid absorbent material to establish a cuff for receiving one end of the pad.

2. The garment of claim 1, including
    an undergarment; and
    at least one fastener on the undergarment to releasably couple the urinal and undergarment together.

3. The garment of claim 2, wherein said fastener comprises filamentary fastener material.

4. The garment of claim 2, wherein said fastener is positioned on said outer piece of fluid resistant material for coupling to said undergarment.

5. The garment of claim 1, wherein said elastic opposite side is formed by an elastic trim.

* * * * *